United States Patent [19]
Jooste

[11] Patent Number: 5,389,384
[45] Date of Patent: Feb. 14, 1995

[54] STERILIZING OR DISINFECTING COMPOSITION

[75] Inventor: Francois Jooste, Beamsville, Canada

[73] Assignee: Trans Delta Corporation, Pickering, Canada

[21] Appl. No.: 546,809

[22] Filed: Jul. 2, 1990

Related U.S. Application Data

[63] Continuation of Ser. No. 302,609, Jan. 27, 1989, abandoned.

[51] Int. Cl.$^6$ ............... A01N 59/08; A01N 59/22; A01N 59/02; A01N 59/00
[52] U.S. Cl. ............... 424/661; 424/663; 424/667; 424/710; 424/711; 424/723; 514/970; 514/973
[58] Field of Search ............ 424/661, 662, 663, 664, 424/667, 723, 710, 711; 514/936, 970, 973

[56] References Cited

U.S. PATENT DOCUMENTS

| | | | |
|---|---|---|---|
| 2,662,855 | 9/1950 | Kamlet | 424/661 |
| 3,084,995 | 4/1963 | Grubitsch | 423/265 |
| 3,123,521 | 3/1964 | Wentworth et al. | 424/615 |
| 4,104,190 | 8/1978 | Hartshorn | 424/663 |
| 4,187,293 | 2/1980 | Nelson | 424/661 |
| 4,239,622 | 12/1980 | Ridgway | 424/664 |
| 4,248,827 | 2/1981 | Kitko | 422/37 |
| 4,839,079 | 6/1989 | Wainberg et al. | 252/106 |

FOREIGN PATENT DOCUMENTS

| | | | |
|---|---|---|---|
| 7659387 | 2/1989 | Australia | A01N 59/08 |
| 0238878 | 9/1987 | European Pat. Off. | B65D 81/32 |
| 0261466 | 3/1988 | European Pat. Off. | B65D 81/32 |

OTHER PUBLICATIONS

Chemical Abstracts, vol. 111, No. 12, Sep. 1989, (Columbus, Ohio, US), see p. 127, abstract 99434q, & JP, 6401798 Shimizu, Kenji et al. 1989.

*Primary Examiner*—Raymond J. Henley, III
*Assistant Examiner*—K. Weddington

[57] ABSTRACT

The present invention provides for a stabilized solution containing a halogen containing compound which is effective as a sterilizing or disinfecting agent, and a stabilizing agent which suppresses the chemical dissociation of the halogen compound such that the sterilizing capability of the solution is maintained for extended periods of time relative to the solution without the stabilizing agent. The halogen containing compound is selected from the group consisting of chlorine dioxide, bromine oxide, bromine chloride, monochloroamine, bromic acid, iodine monochloride, iodine trichloride and iodine monobromide. The stabilizing agent is a compound having at least one accessible sulphur containing group selected from the group consisting of cyclamic acid, dimethyl sulphoxide, glyoxyl sodium bisulphite, potassium sorbate, sodium cyclamate, sodium metabisulphite, sodium oxalate, sodium sulphite, sodium thiosulphate and thioacetamide. Processes and kits for sterilizing or disinfecting water and objects utilizing the stabilized solutions are also provided by the present invention.

16 Claims, 2 Drawing Sheets

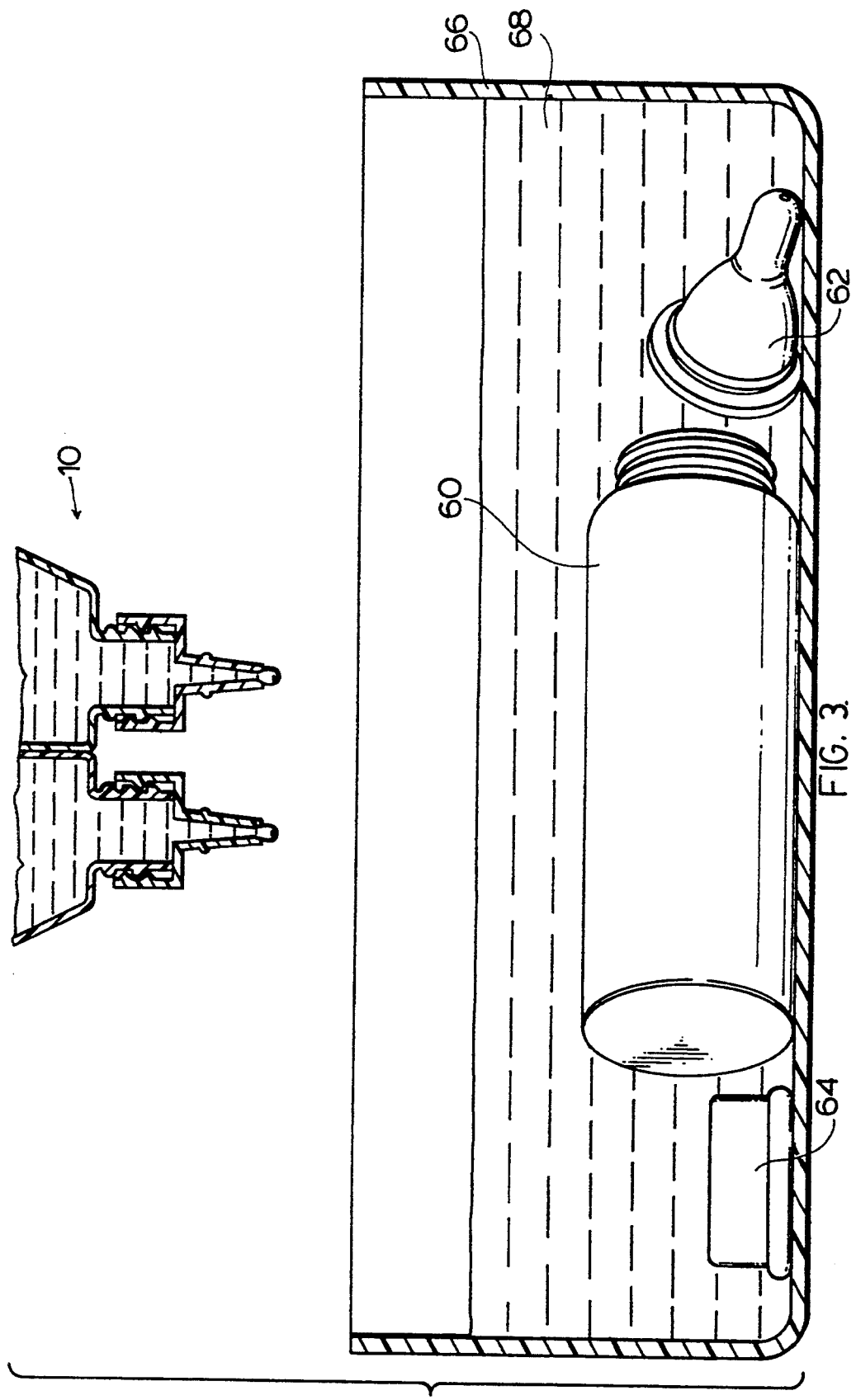

STERILIZING OR DISINFECTING COMPOSITION

FIELD OF THE INVENTION

This application is a continuation of Ser. No. 07/302,609, filed Jan. 27, 1989, now abandoned.

The present invention relates to a composition, method and apparatus useful for disinfecting or sterilizing water, and objects in contact with the water.

BACKGROUND OF THE INVENTION

In many household and other non-industrial situations, it is necessary or desirable to sterilize or disinfect water as well as certain objects. For example, with infants up to six months of age, it is generally recommended to disinfect or sterilize the formula fed to the infant as well as the bottles including the nipples which are used during feeding. As another example, when camping many sources of drinking water, e.g. lakes, streams, etc. may be contaminated with potentially harmful organisms. Similarly, international travellers may be susceptible to microorganisms found in water in various locations.

The term "sterilization" generally denotes the process of eliminating all viable microorganisms from a material, including the spores of the microorganism. In contrast, the term "disinfection" generally refers to the process of destroying, or sometimes merely reducing, the potential infectivity of the material and does not necessarily imply the removal of all viable microorganisms and their spores.

At the present time, the most commonly employed household or other non-industrial methods of disinfection or sterilization are the use of heat and of chemical agents. In the case of heat, the most commonly employed household or non-industrial application uses boiling water. In the case of chemical agents, the most commonly utilized techniques use chlorine gas generating solutions and tablets. Thus, for example in the case of drinking water when camping, potable water is produced either by boiling the water for up to twenty minutes or by adding a chlorine gas generating tablet to the water. In the case of baby bottles, they are generally disinfected by being maintained in a boiling water bath for from five minutes up to about twenty minutes.

The use of boiling water has numerous disadvantages as it can be a tedious or inconvenient procedure, because of the amount of time necessary to disinfect the water. The use of boiling water may also be somewhat dangerous because of the potential for scalds from boiling water baths. Additionally, the use of boiling water for disinfection of baby bottles may result in deterioration of the nipples and clouding of the plastic bottles caused by tiny cracks which may harbor microorganisms which may be difficult to remove.

It is often believed that the use of boiling water results in sterilized water. However, in fact the water may often be only disinfected and not sterilized. For instance, depending upon how long a period of time the water is boiled, some microorganisms may not be killed or inactivated. Boiling water will also generally not kill or inactivate all of the spores of such microorganisms which generally remain viable at about 100° centigrade, the maximum temperature of boiling water under normal conditions. In some applications, there is the potential of the spores continuing to cause some health problems. The spores can germinate to form viable organisms, which if present in small numbers are generally not a major problem. However, if the disinfected solution, for example baby formula, is maintained for extended periods at certain temperatures even a small number of organisms can rapidly multiply and may result in potentially serious illnesses.

There have been attempts, such as the chlorine gas generating tablet described above, to develop cold sterilizing and disinfecting methods which can be used in household or other non-industrial applications. These methods rely on the use of various chemical agents, but still such methods suffer from a number of disadvantages. One such method, for example, requires the use of sodium hypochlorite and other chlorine gas generating solutions. These solutions result in the release of free chlorine gas into the water, which in certain applications can present problems. Chlorine gas is objectionable since in aqueous solution it forms hypochlorous acid, it has a very sharp odor in concentrations as low as 3.5 p.p.m., it is extremely corrosive and it forms toxic and possibly carcinogenic organohalogen compounds, while causing irritation of the pulmonary mucosa. In order to avoid most of these problems the water must be left for a sufficient period to allow the chlorine gas to dissipate. When using these methods with baby bottles, the bottles and nipples are generally rinsed afterward to remove any traces of chlorine and other by-products, with the result that the bottle can be reinfected, thereby defeating the disinfection process.

A number of halogen containing compounds, such as, for example, chlorine dioxide, bromine oxide, bromine chloride, monochloroamine, bromic acid, hypochlorous acid, chlorates, chlorites, hypochlorites, iodine monochloride, iodine trichloride and iodine monobromide among others, are known to be effective disinfecting and sterilizing agents if applied in the proper concentrations. In particular, chlorine dioxide has been used for many years in treatment of municipal water supplies and has recently been demonstrated to be effective as a medical and dental equipment sterilizer, as a disinfectant and deodorizer for beds, as a fungicide, as a toothpaste additive used to prevent dental caries, and as a mouthwash additive.

Chlorine dioxide has been demonstrated to result in the destruction of many microorganisms and their spores at strengths as low as 0.75 p.p.m., as little as 1 p.p.m. of chlorine dioxide in solution killing or inactivating 99,999 of 100,000 *Escherichia coli* bacteria upon contact for five minutes. Chlorine dioxide has also been shown to be effective in inactivating among others, bacteria such as, *Bacillus anthracoides, B. subtilis, B. cereus, B. stearothermilus, B. mesentericus, B. megatherium, Clostridium perfringens, Erberthella typhosa, Haemophilus influenzae, Shigella dysenterie, Salmonella paratyphi B, Salmonella typhosa, Pseudomonas aeruginosa* and *Staphylococcus aureus*; protozoa and algae such as *Naegleria gruberi*; and viruses such as HTLV-III, poliovirus, echovirus, Coxsackie virus, Herpes simplex virus, Newcastle disease virus, Sendaivirus, Vaccinia virus, bacteriophage f2, coliphage and phage $\phi$X 174.

However, some of such halogen containing compounds, such as chlorine dioxide, bromine oxide, bromine chloride and monochloroamine, among others, are generally unstable and there have been a number of problems associated with such instability. In particular, the use of chlorine dioxide is somewhat problematic because at 25° centigrade it exists as a yellow gas which is explosive and may detonate under certain conditions. Thus, chlorine dioxide, being readily soluble in water, is usually stored as an aqueous solution at a low temperature to reduce its instability. Such halogen containing compounds, (e.g. chlorine dioxide, bromine oxide, monochloroamine and bromine chloride, and in particular, chlorine dioxide), however, even in solution, remain generally unstable, in the sense that they have relatively high rates of chemical breakdown or dissociation, particularly in the presence of light. These high rates of chemical breakdown or dissociation render them inefficient and sometimes totally ineffective.

In order to reduce the dissociation of such compounds in solution and take advantage of their excellent sterilization properties, there have been attempts either to provide stable solutions of such compounds or to generate such compounds at their place and time of use. For industrial or commercial applications having the necessary equipment and other resources, the chlorine dioxide is generally produced and used immediately. With household or other non-industrial applications it is not cost effective, feasible or safe to do this. There have thus been attempts to provide stable chlorine dioxide solutions as evidenced by U.S. Pat. Nos. 3,123,521, 3,585,147 and 3,591,515 among others. In most of these situations, the chlorine dioxide is provided by releasing the gas by acidification of solutions in which the chlorine dioxide is made more stable by the addition of a peroxygen or boron compound. While this does result in an increase in the effective shelf life of such chlorine dioxide generating solutions, there is still significant spontaneous breakdown of the chlorine dioxide and, consequently, the sterilizing capacity of the solution is rapidly diminished.

In view of problems, such as noted above, satisfactory methods of storing and/or transporting such halogen containing compounds which allow them to retain their disinfecting or sterilizing properties have not been readily available. The result has been that it has thus not always been possible to utilize to its full potential the excellent disinfectant and sterilizing capability of chlorine dioxide and other such unstable halogen containing compounds, particularly in household and other non-industrial applications.

SUMMARY OF THE INVENTION

The present invention provides for a stabilized solution containing a halogen containing compound which is effective as a sterilizing or disinfecting agent, and a stabilizing agent which suppresses the chemical dissociation of the halogen compound such that the sterilizing capability of the solution is maintained for extended periods of time relative to the solution without the stabilizing agent.

In an aspect of the invention a process is provided for sterilizing water and any object in contact with the water comprising, adding to the water the stabilized solution and an activator such that the sterilizing agent of the stabilized solution is released or generated, thereby rapidly sterilizing the water and objects in contact with the water.

In another aspect of the invention, an indicator is provided to directly monitor the sterilization process.

In yet another aspect of the invention, a kit is provided for sterilizing water and objects in contact with the water comprising a container holding the stabilized solution, and an activator for releasing or generating the sterilizing agent.

As a result of the compositions and methods above, it is now possible to utilize more fully the excellent disinfectant and sterilizing capability of halogen containing compounds, such as chlorine dioxide, particularly in household and other non-industrial applications.

BRIEF DESCRIPTION OF THE DRAWINGS

The above as well as other advantages and features of the present invention will be described in greater detail according to preferred embodiments of the present invention in which;

FIG. 3 is a cross-sectional view of the apparatus of FIG. 1 in use in sterilizing a baby bottle.

DETAILED DESCRIPTION OF THE INVENTION

Figure 1:
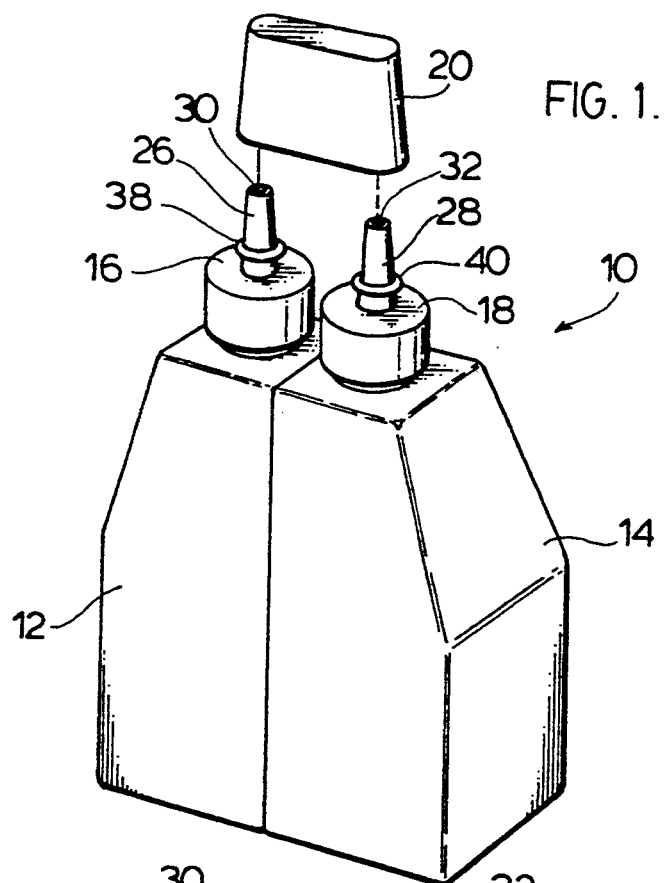
FIG. 1 is a perspective view of the preferred apparatus of the present invention.

The present invention makes use of a halogen containing compound which is effective as a sterilizing or disinfecting agent. Such halogen containing compounds include chlorine dioxide, bromine oxide, bromine chloride, monochloroamine, bromic acid, iodine monochloride, iodine trichloride and iodine monobromide. Preferably, because of their effectiveness, the halogen containing compound shall be such that the sterilizing agent is chlorine dioxide, bromine oxide, bromine chloride or monochloroamine, and most preferably because of its effectiveness and safety, chlorine dioxide.

In general, the halogen containing compound which is to be used in the stabilized solution can be prepared by any of the processes known in the art for manufacturing or synthesizing such components. Thus, in the case of chlorine dioxide, chlorine dioxide gas is prepared by any of the known processes for manufacturing or synthesizing chlorine dioxide and then later converting it into a gas. Among such methods and processes are those disclosed in Kirk-Othmer, *Encyclopedia of Chemical Technology*, Vol. 5, pages 615-617; and *Chlorine Dioxide: Chemistry and Environmental Impact of Oxychlorine Compounds* by W. S. Masschelein, Ann Arbor Science Publishers, Inc., (1979) pages 9-11 and 112-140, the relevant portions of which are incorporated herein by reference.

Once manufactured, the chlorine dioxide should preferably be purified to remove all traces of free chlorine. There are several well known techniques for accomplishing this purification, as for example, a chlorine scrubber which involves passing the chlorine dioxide gas through a column containing either arsenite or solid sodium chlorite or a concentrated sodium chlorite solution, as described for example in Masschelein, *supra*, pages 135-138, the relevant portions of which are incorporated herein by reference. When passing the chlorine dioxide gas through the scrubber, it is mixed with an inert gas such as nitrogen to reduce the possibility of explosion as well as to act as a diluent or carrier. The inert gas also acts to prevent the undesired dissociation of the chlorine dioxide by the presence of oxygen or air thereby preventing formation of undesirable by-products such as chlorine gas.

The invention also makes use of a stabilizing component which increases the stability of the halogen containing compound in solution by suppressing the chemical dissociation of the halogen containing compound and/or the sterilizing agent in the solution. Compounds useful as stabilizing components have an available group which is believed to complex loosely with the halogen in the halogen containing compound, thereby stabilizing the halogen containing compound. Such compounds include for aqueous and non-aqueous solutions those having sulphur containing groups (such as thio groups, sulphamyl groups, sulphate groups and sulphite groups, among others), hydroxyl groups, carboxyl groups and oxo groups. For aqueous solutions salts of these compounds, for example the sodium or potassium salts are generally preferred. Particularly useful such compounds are those having an available sulphur such as, for example, cyclamic acid or its salts, preferably sodium cyclamate, sorbic acid and its salts, oxalic acid and its salts, dimethyl sulphoxide and thioacetamide. Most preferred are cyclamic acid, dimethyl sulphoxide, glyoxyl sodium bisulphite, potassium sorbate, sodium cyclamate, sodium metabisulphite, sodium oxalate, sodium sulphite, sodium thiosulphate and thioacetamide. Such compounds however should not have a group which is reactive with the halogen containing compound. In the case of chlorine dioxide, such reactive groups include, among others, free amine groups and accessible unsaturated carbon bonds.

In this specification, the term "stabilized solution" shall be understood to mean a solution of a halogen containing compound in combination with a stabilizing component.

In the preferred embodiment, chlorine dioxide is generated as the sterilizing agent by acidification of a stabilized chlorine dioxide solution. The stabilized chlorine dioxide solution may be provided as either an aqueous or alcoholic solution.

It has been found that, when the chlorine dioxide is provided as an aqueous solution, it may be advantageous to add to the solution compounds (such as borate or peroxygen compounds) which may aid in increasing the concentration of the chlorine dioxide which may be dissolved in the solution. The process for producing the reaction products of chlorine dioxide with the boron compounds are disclosed in, for example, U.S. Pat. No. 2,701,781. The peroxygen compounds are disclosed in, for example, U.S. Pat. Nos. 3,123,521 and 3,585,147. The relevant portions of the disclosures of said patents are incorporated herein by reference. Particularly preferable are alkaline peroxygen compounds, in particular alkaline metal peroxygen compounds such as sodium carbonate peroxide or hydrogen peroxide with alkaline carbonates and bicarbonates.

Aqueous forms of the stabilized solution capable of generating chlorine dioxide as the sterilizing agent are preferably prepared by dissolving an alkali metal peroxygen compound or compounds in water to form an aqueous solution containing about 5 percent w/w, to about 15 percent w/w, and preferably about 10 percent w/w, of the peroxygen compounds. The stabilizing component, preferably sodium cyclamate, is dissolved in the peroxygen solution at a concentration of about 2 percent w/w, to about 10 percent w/w, preferably between about 3 percent w/w, to about 7 percent w/w, and most preferably 5 percent w/w. Chlorine dioxide gas is then bubbled through the solution under an inert gas atmosphere, e.g. nitrogen, helium, or even carbon dioxide under special circumstances, but preferably nitrogen or helium, until preferably at least about 40,000 p.p.m. and most preferably about 50,000 p.p.m. of chlorine dioxide is absorbed therein. For good stability, the aqueous solutions should be maintained at a pH value above 7, preferably between about 7.8 and 9.5, most preferably between about 8.8 and 9.2.

Non-aqueous solutions are prepared in any suitable organic solvent, preferably an alcohol, most preferably a lower alkyl alcohol. Such solutions are prepared by dissolving cyclamic acid in an alkyl alcohol, preferably methanol or ethanol, at a concentration of about 2 percent w/w to about 10 percent w/w, preferably between about 3 percent w/w to about 7 percent w/w, and most preferably about 5 percent w/w. Thereafter, chlorine dioxide gas is bubbled through the solution under a similar inert gas atmosphere until preferably at least about 40,000 p.p.m. and most preferably about 50,000 p.p.m. of chlorine dioxide is absorbed therein.

The resulting stabilized solution can be titrated using standardized techniques to determine the amount of chlorine dioxide present as, for example, those disclosed in Kirk-Othmer, *supra*, pages 617–618, the relevant portions of which are incorporated herein by reference. Other techniques such as gas chromatography may also be employed.

The halogen containing compound is generally released from the stabilized solution by the action of an activator added to the solution. The activator for the solution is a compound which, when mixed with the solution, will cause the release of the halogen containing compound in the solution. For example, when releasing chlorine dioxide from the stabilized chlorine dioxide solution, an activator which will lower the pH of the stabilized solution to below pH 7, and preferably to at least as low as pH 6, will result in the release of chlorine dioxide in the solution.

In such circumstances, acidic solutions in the pH range of about 2 to about 6 are preferably utilized as activators. Such solutions can include solutions of any of the common inorganic or organic acids such as, for example, hydrochloric acid, sulphuric acid, phosphoric acid, sorbic acid, acetic acid and citric acid which will cause the release or generation of the sterilizing agent from the solution. Also useful as activators are metal acids e.g. aluminum sulphate, aluminum chloride, ferric chloride, ferric sulphate, ferrous chloride, ferrous sulphate, etc. which can be in combination with an organic acid such as citric acid, sorbic acid or glucose acid. A preferable mixture of sorbic acid or citric acid with aluminum chloride or aluminum sulphate will also aid in removal of organic and inorganic deposits such as calcium deposits and milk residues very often found in baby bottles.

Alternatively, the activator can be provided in a powdered activator preparation, which may conveniently be pressed into a tablet. In this case, the activator chosen is one which is available in a powder or crystal form. Particularly suitable are organic acids such as citric acid, sorbic acid, etc. The powdered activator preparations and in particular the tablets are preferably effervescent, so as to aid in the rapid disposition of the activator throughout the water. The manufacture of such tablets or powder or granules can be accomplished by any of the common methods known in the art. For example, the provision of a weak alkali (e.g. sodium bicarbonate) which will react with some of the acid and release an inert gas is effective for effervescence. In such situations the concentration and amount of acid in the activator is adjusted to compensate for the reaction with the weak alkali.

The concentration of acids in the activator solution or powder is dependent upon numerous factors such as:

the desired pH of the sterilizing or disinfecting process e.g. the end pH is preferably less than about pH 6 in order to provide rapid release of sufficient amounts of the sterilizing agent; the amount of liquid used in the sterilization process into which the stabilized solution and activator solution or powder are to be added; the amount of stabilized solution which is to be added in the sterilizing or disinfecting application; the starting pH of the stabilized solution; the Ka value of the acid employed and how much acid is needed to break through the buffer threshold of the stabilized solution and achieve the desired pH. The determination of the concentration of the activator taking into account the above factors will be known to those of ordinary skill in the art.

In order to compensate for any possible errors in dispensing of the proper amounts of stabilized solution and activator, especially in a household application, between about 10% and about 100% excess acid than is indicated by the theoretical considerations and preferably about 25% excess may be used.

A preferable acid activator solution is a 10% w/w aqueous solution of a equimolar mixture of citric acid and aluminum chloride or aluminum sulphate, which has a pH value of 1.8. Of this solution, one can add about 2 ml to about 4 ml, preferably about 2.5 ml, per liter of water to be sterilized or disinfected. To the water will then also be added about 2 ml to 3 ml, preferably about 2.5 ml of a stabilized solution containing about 40,000 to 50,000 p.p.m. concentrate of the halogen containing compound which will yield 100 to 125 p.p.m. final concentration of the sterilizing agent. Theoretically, 2 ml of the above acid activator solution should easily break through the high pH buffer threshold of the concentrated solution contained in the water.

Preferably, the concentrations of free chlorine dioxide during the sterilization or disinfection process are greater than 2 p.p.m., preferably between 25 p.p.m. and 500 p.p.m., more preferably between 25 p.p.m. and 200 p.p.m., and most preferably between 25 p.p.m. and 150 p.p.m.

For convenience, it may be desirable to provide an indicating system to indicate to the user when the sterilization or disinfection process is completed. The indicator is preferably chosen so that it monitors the sterilization process by monitoring the directly related activity of the sterilizing agent. Indirect monitoring, e.g. by monitoring only the pH change of the sterilizing bath, may not be accurate as the time characteristics of the pH change may be different than those of the sterilization process.

When using chlorine dioxide or any of the other highly reactive halogen containing compounds, as the sterilizing agent, which are known to react, for example, with amine groups, an aminic coloring agent, such as one of the FD&C colors which are typically used as food coloring agents (e.g. red, blue, orange, green or purple food colors) can be added to the activator solution, tablet, or powder. The indicator should be selected such it does not react with the activator. When the chlorine dioxide or other sterilizing agent is generated or released from the stabilized solution, it reacts with the coloring agent and the color of the solution fades and disappears after a short time. Such a reaction, which is selected or adjusted to have a time course similar to or longer than the sterilization reaction, indicates to the user that the sterilization or disinfection process is completed.

In the case of an activator solution, the indicating coloring agent is dissolved in the activator solution, which provides the added benefit of ease of differentiation of the activator and stabilized solutions. In the case of a powdered activator, and in particular a tablet, the indicating coloring agent is provided in powder or crystal form and is incorporated into the activator powder or tablet.

In other embodiments it may be desired to provide an indicator which can be added to a stabilized solution which does not require an activator.

The sterilization or disinfection process is allowed to continue sufficiently long to allow the sterilizing agent to destroy or inactivate to the desired degree any susceptible microorganisms and their spores which may be present. These times vary from about one second to about five minutes or longer, depending on the nature of the organism to be destroyed or inactivated, the concentration of the sterilizing agent present in the water to be sterilized or disinfected, the degree of efficacy desired, the surface area of any objects to be sterilized and the porosity of such surfaces both to microorganisms, their spores and their colonies as well as to the sterilizing agent such as chlorine dioxide.

For use in the sterilization or disinfection process, the stabilized solution is preferably provided as a concentrated solution which is diluted by the user and then activated. For certain applications, it may be desirable to provide pre-measured amounts of the already activated solution e.g. in a sachet or a small bottle containing 1 to 10 ml, preferably 5 ml, the entire contents of which are mixed with the water to be sterilized.

There are numerous applications of the solutions and processes of the present invention. As noted hereinabove, they are useful for sterilizing or disinfecting water and various objects such as medical and dental instruments, baby bottles, baby diapers, etc. The solutions are particularly useful in the disinfection and sterilization of soiled baby diapers, either reusable cloth diapers or in processes for recycling the materials of soiled disposable baby diapers.

Chlorine dioxide is also known to be an effective agent for wound healing as it demonstrates reactivity against *Pseudomonas aeruginosa*, a bacteria which is commonly found as an infective agent of such wounds. For such an application, wound dressings saturated in the activated chlorine dioxide solution can be sealed in pouches or sachets. The addition of the stabilizing component enables such wound dressings to have a long shelf life.

The solutions may also be used in the formulation of fly ash, lime and clay mixtures for the production of building bricks as described in, among others, U.S. Pat. Nos. 4,780,144, 4,501,618 and European Patent Publications 208,070 and 87,474. In such applications the stabilized chlorine dioxide solutions with the citric acid and aluminum salts activators complex heavy metals as well as disinfecting the mixtures preventing particularly fungal growth.

The invention is further exemplified by the embodiment described in the following illustrative and non-limiting example.

DETAILED DESCRIPTION OF A PREFERRED EMBODIMENT OF THE INVENTION

PREPARATION (A)

STABILIZED SOLUTION

A stabilized solution capable of releasing chlorine dioxide when activated was prepared by first dissolving 100 g powdered sodium carbonate peroxide in 900 g water to form a 10% w/w solution. To this solution was added 50 g sodium cyclamate to form a solution containing about 5% w/w sodium cyclamate. Chlorine dioxide in a nitrogen gas diluent, containing essentially no free chlorine, was then bubbled through the solution of sodium carbonate peroxide and sodium cyclamate until approximately 6 mg of gaseous chlorine dioxide was taken up per gram dry weight of sodium carbonate peroxide. The pH of the solution was adjusted to the desired pH, most preferably 8.8 to 9.2 by the addition of sodium hydroxide. The resulting stabilized solution prepared in accordance with this method contained about 50,000 p.p.m. of dissolved chlorine dioxide at a pH value between about 8.8 and 9.2.

PREPARATION (B)

ACTIVATOR SOLUTION

An activator solution was prepared by dissolving 50 g of citric acid and 50 g of aluminum sulphate in 900 g of water. This 10% solution of a mixture containing 50% w/w citric acid and 50% w/W aluminum sulphate had a pH value of about 1.8.

PREPARATION (C)

ACTIVATOR TABLETS

An effervescent powder mix was provided as follows:

| | |
|---|---|
| Aluminum sulphate | 12 g |
| water | 50 g |
| Citric acid monohydrate | 50 g |
| Sodium bicarbonate | 132 g | and formulated into tablets of about 500 mg each.

An additional mixture using Tartaric acid was provided as follows:

| | |
|---|---|
| Citric acid monohydrate | 162 g |
| Tartaric acid dry powder | 200 g |
| Sodium bicarbonate | 477 g | and formulated into tablets of about 500 mg each.

EFFICACY OF THE STABILIZING COMPONENT

A) STABILITY OF THE STABILIZED SOLUTION

Solutions of 10,000 ppm dissolved chlorine dioxide were prepared generally in accordance with the process of Preparation A above. One solution was prepared containing the sodium cyclamate and a control solution was prepared by omitting the sodium cyclamate. The solutions were adjusted to varying pHs from 7.0 to 9.5 and the free chlorine dioxide content of the solutions determined by gas chromatography.

| Control | | With cyclamate | |
|---|---|---|---|
| pH | ppm | pH | ppm |
| 7.0 | 6.0 | 7.0 | 1.5 |
| 7.1 | 5.7 | 7.2 | 1.0 |
| 7.5 | 4.8 | 7.6 | 0.3 |
| 8.0 | 3.7 | 8.0 | 0.0 |
| 8.5 | 2.8 | 8.4 | 0.0 |
| 9.0 | 1.6 | 8.8 | 0.0 |
| 9.5 | 0.5 | 9.5 | 0.0 |

The addition of the cyclamate provided for a solution which was much more stable and contained less free chlorine dioxide. This indicated a reduced dissociation of the chlorine dioxide in the stabilized solution.

B) STABILITY OF THE CHLORINE DIOXIDE GENERATED

Solutions of 40,000 ppm dissolved chlorine dioxide were prepared generally in accordance with the process of Preparation A above. One solution was prepared containing the sodium cyclamate and a control solution was prepared omitting the sodium cyclamate. In order to adequately study the time course of the dissociation of chlorine dioxide, the solutions were activated by adding citric acid as an activator until the pH of the solutions reached 6.5. The solutions were then placed into stoppered bottles with the headspace filled with nitrogen and maintained at 50° centigrade. At various times after the activation, samples were drawn from the bottles, the bottles were re-filled with nitrogen and returned to the 50° centigrade chamber. The samples were analyzed for chlorine dioxide content by gas chromatography and compared with the content of the freshly activated solutions. The following table illustrates the effectiveness of the sodium cyclamate as a stabilizing component for chlorine dioxide once generated. The numbers in columns 2 and 3 indicate the percent of the undissociated chlorine dioxide remaining in the solution:

| Time after Activation (Hours) | With Cyclamate (% ClO$_2$) | Control (% ClO$_2$) |
|---|---|---|
| 0.1 | 100 | 98 |
| 0.2 | 100 | 96 |
| 0.3 | 99* | 93 |
| 0.4 | 100 | 92 |
| 0.5 | 100 | 91 |
| 1.0 | 100 | 74 |
| 1.5 | 100 | 49 |
| 2.0 | 99* | 21 |
| 2.5 | 100 | 3 |
| 3.0 | 100 | 0 |
| 4.0 | 99* | 0 |
| 8.0 | 100 | 0 |
| 12.0 | 100 | 0 |
| 24.0 | 100 | 0 |
| 36.0 | 100 | 0 |

*values within experimental error.

As is illustrated by the table, in the control solution without the cyclamate all of the chlorine dioxide in the solution had dissociated into hypochlorous acid and chlorite after only three hours. Even after only 0.5 hours, a significant amount of the chlorine dioxide had dissociated. In contrast, in the solution containing cyclamate essentially all of the chlorine dioxide remained in the solution even after 36 hours at 50° C. Additionally in the control, as the chlorine dioxide dissociated, the formation of hypochlorous acid accelerated further the dissociation.

DESCRIPTION OF THE PREFERRED APPARATUS OF THE INVENTION AND METHOD OF USE OF THE APPARATUS IN STERILIZING OR DISINFECTING AN ARTICLE

Figure 2:
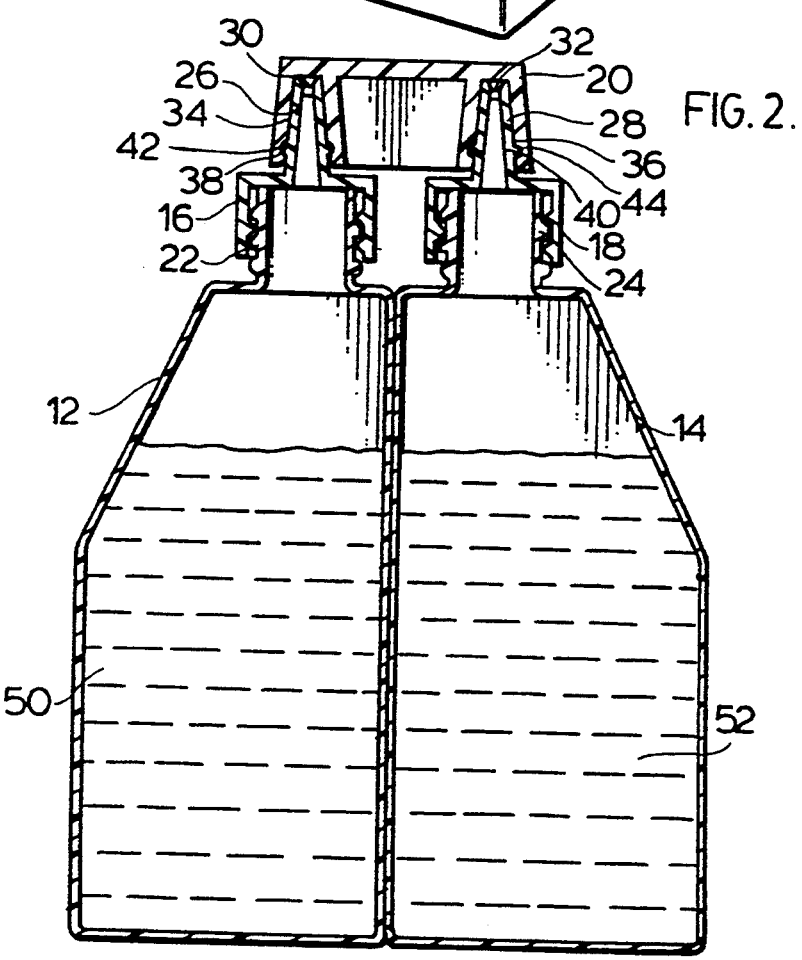
FIG. 2 is a cross-section of the apparatus of FIG. 1.

FIGS. 1 and 2 illustrate a solution dispensing apparatus generally indicated by the numeral 10 embodying the present invention. Apparatus 10 is useful for sterilizing or disinfecting water and various articles, particularly, small articles such as medical and dental instruments and household articles (e.g. baby bottles, thermometers, etc.).

Apparatus 10 comprises two containers 12 and 14 which are held, joined or integrally formed together. The containers 12 and 14 are preferably of a volume to hold up to 250 ml each, most preferably of a volume to hold 50 to 100 ml each. Containers 12 and 14 have, at their top, threaded mouths 22 and 24 onto which individual caps 16 and 18 are threaded. Caps 16 and 18 define generally conically shaped dropping spouts 26 and 28 with openings 30 and 32 therein providing a passage for fluid from the interior of containers 12 and 14 to the external environment. The size of the opening is selected such that a defined amount of the solution can be easily dispensed. In a particular embodiment, the size of openings 30 and 32 is selected such that about 10 to 15 drops provides 1 ml of liquid, preferably 12 drops to provide 1 ml of liquid.

A second cap 20 is provided with complementary chambers 34 and 36 which mate with spouts 26 and 28 thereby sealing openings 30 and 32. Spouts 26 and 28 have locking formations, rings 38 and 40 in the illustrated embodiment, protruding from their exterior surfaces which are adapted to removedly interconnect with complementary formations, i.e. grooves 42 and 44, in cap 20, thereby allowing cap 20 to be locked onto spouts 26 and 28. In order to reduce the possibility of premature mixing of the liquids contained in containers 12 and 14, cap 20 is designed in such a way that it can fit only one way onto spouts 26 and 28, e.g. one of spouts 26 or 28 is larger than the other or the positioning of locking rings 38 and 40 and complementary grooves 42 and 44 differs one to the other.

Container 12 holds a stabilized solution 50, which in the preferred embodiment is a stabilized solution capable of releasing chlorine dioxide at a concentration of about 50,000 p.p.m. of dissolved chlorine dioxide at a pH value between 8.8 and 9.0 as prepared by the process described above. Container 14 holds an activator solution 52. In the embodiment shown, container 14 holds a solution of citric acid and aluminum sulphate having a pH value of about 1.8.

FIG. 3 illustrates the use of the liquid dispensing apparatus 10 of the present invention in sterilizing small objects, such as a baby bottle 60, nipple 62 and nipple retainer ring 64. The bottle 60, nipple 62 and ring 64 are placed in a container 66 containing water 68. The volume of water should be sufficient to completely cover bottle 60, nipple 62 and ring 64. The cap 20 of apparatus 10 is removed and apparatus 10 inverted water 68. Sufficient volumes of each of the stabilized solution 50 and the activator solution 52 are dispensed into the water 68 such that when mixed together an adequate concentration of the sterilizer component is released into the water to cause sterilization of bottle 60, nipple 62 and ring 64. In the preferred embodiment, with a stabilized solution containing about 50,000 p.p.m. of dissolved chlorine dioxide at a pH value between 8.8 and 9.0, 1 to 3 ml of the stabilized solution per liter of water, provides adequate concentrations of free chlorine dioxide for rapid sterilization once activated. With the apparatus as shown about 12 drops of the chlorine dioxide solution is about 1 ml.

In the preferred embodiment, with a bath containing about 2 liters of water, 2 ml to 8 ml of the activator solution, preferably 5 ml is added to the 2 liter bath containing the bottles. To this bath will then be added about 5 ml of 50,000 p.p.m. concentrate which will yield about 125 p.p.m. of chlorine dioxide.

Alternatively, with some designs of baby bottles, bottle 60 may be filled with water, the stabilized sterilizer solution and activator solutions are dropped into the water, the nipple inverted and placed into the bottle covered by the nipple retainer ring and the bottle shaken to result in sterilization of the bottle.

While the invention has been described in reference to the specific embodiments, it should be understood by those skilled in the art that various changes can be made and equivalents can be substituted without departing from the true spirit and scope of the invention. All such modifications are intended to be within the scope of the claims appended hereto.

What is claimed is:

1. In a solution containing at least 40,000 p.p.m. of a halogen containing compound which is effective as a sterilizing or disinfecting agent said halogen containing compound being selected from the group consisting of chlorine dioxide, bromine oxide, bromine chloride, monochloroamine, bromic acid, iodine monochloride, iodine trichloride and iodine monobromide, the improvement comprising the addition of about 2 to about 10 percent by weight based upon the total weight of the solution of a stabilizing agent which suppresses the chemical dissociation of the halogen containing compound such that the sterilizing capability of the solution is maintained for extended periods of time relative to the solution without the stabilizing agent, said stabilizing agent being a compound selected from the group consisting of cyclamic acid, dimethyl sulphoxide, glyoxyl sodium bisulphite, potassium sorbate, sodium cyclamate, sodium metabisulphite, sodium oxalate, sodium sulphite, sodium thiosulphate and thioacetamide.

2. A solution as claimed in claim 1 wherein said solution is an aqueous solution having a pH greater than about 7.

3. A solution as claimed in claim 2 wherein said halogen containing compound is chlorine dioxide.

4. A solution as claimed in claim 3 wherein said stabilizing agent is sodium cyclamate.

5. A solution as claimed in claim 4 wherein said solution has a pH in the range of about 7.8 to about 9.5.

6. A solution as claimed in claim 1 wherein said halogen containing compound is selected from the group consisting of chlorine dioxide, bromine oxide, bromine chloride and monochloroamine.

7. A solution as claimed in claim 6 wherein said solution is an aqueous solution having a pH less than about 7.

8. A solution as claimed in claim 6 wherein said stabilizing agent is sodium cyclamate.

9. A solution as claimed in claim 7 wherein said halogen containing compound is chlorine dioxide.

10. A solution as claimed in claim 9 wherein said solution has a pH in the range of about 6.0.

11. A solution as claimed in claim 1 wherein said stabilizing agent is present in a concentration of about 3 to about 7 percent weight by weight.

12. A solution as claimed in claim 11 wherein said halogen containing compound is chlorine dioxide.

13. A solution as claimed in claim 12 wherein said stabilizing agent is sodium cyclamate.

14. A solution as claimed in claim 11 wherein said stabilizing agent is present in a concentration of about 5 percent weight by weight.

15. A solution as claimed in claim 14 wherein said halogen containing compound is chlorine dioxide.

16. A solution as claimed in claim 15 wherein said stabilizing agent is sodium cyclamate.

* * * * *